United States Patent [19]

Nentwig et al.

[11] Patent Number: 4,987,075

[45] Date of Patent: Jan. 22, 1991

[54] METHOD OF MAKING AN ENZYME MEMBRANE FOR ENZYME ELECTRODES

[75] Inventors: Jürgen Nentwig, Berlin; Frieder Scheller, Zepernick; Günter Hanke, Schwerin; Wolfgang Breitmoser, Wittenberge; Hartmut Weise; Dorothea Pfeiffer, both of Berlin; Anette Nünchert, Babelsberg; Florian Schubert, Berlin; Christoph Meiske, Schwaneback; Siegfried Kühnel, Dresden, all of German Democratic Rep.

[73] Assignee: Akademie der Wissenschaften, Berlin, Fed. Rep. of Germany

[21] Appl. No.: 555,788

[22] Filed: Jul. 19, 1990

Related U.S. Application Data

[63] Continuation of Ser. No. 455,916, Dec. 21, 1989, abandoned, which is a continuation of Ser. No. 219,585, Jul. 15, 1988, abandoned.

[30] Foreign Application Priority Data

Jul. 23, 1987 [DD] German Democratic Rep. .................................... 3042802

Jul. 23, 1987 [DD] German Democratic Rep. .................................... 3052816

[51] Int. Cl.$^5$ ............................................ G01N 27/30
[52] U.S. Cl. .............................. 435/182; 204/153.12; 204/403; 435/179; 435/288
[58] Field of Search ............... 435/817, 291, 288, 180; 204/153.12, 403, 182, 179; 428/423.1

[56] References Cited

U.S. PATENT DOCUMENTS

| | | | |
|---|---|---|---|
| 3,539,455 | 11/1970 | Clark | 204/408X |
| 3,905,923 | 9/1975 | Klug | 428/423.1 X |
| 3,929,574 | 12/1975 | Wood et al. | 435/43 |
| 3,948,745 | 4/1976 | Guilbault et al. | 204/403 |
| 4,240,889 | 12/1980 | Yoda et al. | 204/403 |
| 4,312,946 | 1/1982 | Wood et al. | 435/182 |
| 4,342,834 | 8/1982 | Wood et al. | 435/182 |
| 4,388,166 | 6/1983 | Suzuki et al. | 204/403 |
| 4,757,014 | 7/1988 | Hendrickson et al. | 435/180 |

FOREIGN PATENT DOCUMENTS 1442303  7/1976  United Kingdom ............... 204/1 E

*Primary Examiner*—G. L. Kaplan
*Attorney, Agent, or Firm*—Schweitzer, Cornman & Gross

[57] ABSTRACT

The inventive membrane of high selectivity comprises a laminated enzyme membrane, which is enclosed by two cellulose membranes. The laminated enzyme membrane is an enzyme-containing polyurethane layer; the cellulose membranes are coated with cellulose nitrate.

The inventive process is characterized in that ferricyanide or hydrogen peroxide is added in the presence of peroxidase to the measurement sample, the measurement portion or the enzyme membrane.

8 Claims, No Drawings

METHOD OF MAKING AN ENZYME MEMBRANE FOR ENZYME ELECTRODES

This is a continuing application of U.S. Ser. No. 455,916, filed on Dec. 21, 1989, which is a continuation of U.S. Ser. No. 219,585, filed on July 15, 1988, both now abandoned.

FIELD OF THE INVENTION

The invention is directed to a modified enzyme membrane having high selectivity for enzyme electrodes and methods for their application, for example, for use in the determination of glucose, lactate, sucrose or uric acid in physiological solutions, fermentation samples, as well as in beverages and foods. The invention can be used in clinical diagnosis, in the food industry in fermentation control and in environmental protection.

BACKGROUND OF THE INVENTION

Enzyme electrodes are based on coupling the reaction of the substrate to be determined under the action of immobilized enzymes with the electrochemical indication of an electrode-active partner of the enzyme reaction While enzyme reactions generally have a high selectivity, the electrochemical indication reaction, coupled to these reactions, generally is relatively nonspecific. The cause of this nonspecificity lies in the electrochemical reaction of all components of the test sample with a conversion potential below the potential of the indicator electrode. These interferences are excluded by permselective membranes, which are disposed either directly before the indicator electrode (U.S. Pat. No. 3,979,274) or between the test solution and the enzyme layer (Toshiba Rev. 132). These membranes have a selective permeability because of the pore exclusion volume or the charge on the permeant. Nevertheless, molecules with a molecular weight similar to that of the substances indicated at the electrode can lead to interference. Moreover the manufacture of such permselective membranes is expensive and the use in enzyme electrodes is inappropriate because of mechanical instability.

A different principle of excluding these interferences is based on measuring the difference between an enzyme-free indicator electrode an enzyme-loaded indicator electrode (German Federal Republic Pat. No. 1,598 285). Admittedly, this method permits the exclusion of the effect of interfering substances of the measurement sample. However, it requires very expensive equipment and frequent calibrations. Moreover, the method is unsuitable for "kinetic methods of measuring", since the kinetic behavior of these two different electrodes is different.

It has furthermore been proposed that the interfering substances of the test sample be removed by means of an enzymatic reaction in an additional layer before the actual enzyme layer. This method requires a specific enzyme for each interfering substance and is therefore suitable for use only in those test samples, which always contain the same interfering substances.

To achieve correct measurements with a laminated enzyme membrane, the enzyme layer was disposed between two semipermeable membranes. Although all species up to a molecular weight of 15,000 Dalton can pass through this laminated membrane, low concentrations of interfering substances do not cause any falsification of the values measured, since the $H_2O_2$ formed in the enzyme reaction permeates significantly more rapidly through the enzyme layer and the second dialysis membrane. On the other hand, when determining urine glucose where the concentration of the interfering substances may be appreciably higher than that of the substances being analyzed, excessively high measurement values occur frequently.

Moreover, a bienzyme electrode is known (German Democratic Republic Pat. No. 236 553), which contains an enzyme (indicator enzyme), which converts the substance to be determined into an electroactive product, as well as an enzyme (eliminator enzyme), which converts the interfering substances into substances which do not interfere electrochemically. Interfering substances, which are not converted effectively by the eliminator system can be converted in the measurement solution by an upstream chemical reaction into substances, which do not interfere, and an interfering substance, which is a substrate of the eliminator enzymes. The effect of interfering substances was partially suppressed even by an additional eliminator electrode. The difference measurement and the use of an eliminator electrode require additional expense for equipment and are therefore appreciably more expensive than simple measurements. Moreover, the eliminator electrode does not lead to the complete exclusion of interference. The membranes described are also very expensive and, at the same time, very thin and not very stable.

The measurements are slowed down significantly through the use of several superimposed enzyme layers For this reason, they are not suitable for use in the conventional analyzers.

Furthermore, the functional stability of the eliminator enzyme frequently is decreased drastically by products of the indicator enzyme reaction, such as $H_2O_2$.

DESCRIPTION OF THE INVENTION

It is an object of the invention to develop a modified membrane with high selectivity for enzyme electrodes and a method for its use. A falsification of the results of the measurements by the different electrode active interfering substances contained in the respective measurement sample shall be excluded. The membrane shall be distinguished by a good mechanical stability and be reasonably priced.

The enzyme membrane, modified pursuant to the invention, comprises a laminated enzyme membrane which is enclosed on both sides by a cellulose membrane. The two cellulose membranes are coated with cellulose nitrate by treatment with a cellulose nitrate solution. The laminated enzyme membrane is connected by means of diisocyanate, triisocyanate or polyisocyanate with the two cellulose membranes. This laminated enzyme membrane comprises a polyurethane layer, which encloses enzymes. Individual enzymes and, optionally, finely divided low molecular weight substances, which affect enzymatic reactions, but also enzyme mixtures and substance mixtures may be contained. For a total thickness of the laminate of about 25 $\mu m$, the particle size of the enzymes should be less than 15 $\mu m$. A particularly advantageous embodiment of the laminate has an average particle size of less than 1 $\mu m$.

As enzymes, suitably glucose oxidase, lactate oxidase, glutamate oxidase, sarcosine oxidase, urate oxidase or mutarotase are used.

The polyurethanes used suitably comprise polyester alcohols, chain extenders and diphenylmethane diisocyanate, as well as crosslinkable groups.

The inventive enzyme membrane is produced by embedding an enzyme in a polyurethane system and covering it with two cellulose membranes. The sandwich membrane, so produced, is sprinkled on both sides with cellulose nitrate solution and is subsequently dried.

This modification leads to a retardation of the permeation of charged substances, while the transport of the product of the enzymatic reaction —$H_2O_2$—is retarded only insignificantly. For this reason, only the L course of the formation of $H_2O_2$ is detected in kinetic measurements.

The method to improve the selectivity by using the inventive membrane for enzyme electrodes, based on the $H_2O_2$ reading, is characterized in that the interfering substances are oxidized using ferricyanide or hydrogen peroxide in the presence of peroxidase (POD) which are added to the test sample, the test portion or the enzyme membrane The interfering substances, which otherwise are oxidizable at the electrode, are oxidized already in the measurement portion to noninterfering substances. If $H_2O_2$ is used, the decomposition of the unreacted residual $H_2O_2$ is achieved before the measurement by the addition of catalase or an excess of ferrocyanide. Due to the POD already used for the oxidation of the interfering substances there is rapid decomposition of the $H_2O_2$ with formation of ferrocyanide. On the other side the spontaneous reaction of $H_2O_2$ with ferrocyanide is so slow that there is no interference with the measured value due to the consumption of the $H_2O_2$ formed in the enzyme reaction. The excess of ferrocyanide when $H_2O_2$ is used, or the ferrocyanide formed when ferricyanide is used as oxidizing agent does not interfere with the measurement of the substances to be determined when the nitrocellulose-modified enzyme membrane is used.

The inventive membrane has good mechanical stability, is well priced since no eliminator system is required and has a long troublefree functional stability. The invention is described in the following by means of examples.

EXAMPLE 1

Glucose oxidase is immobilized as follows. To 1 mL of a solution of 0.5 g polyurethane system Syspur K 8010® in 100 mL of acetone, 4,000 units of glucose oxidase are added and homogenized (vigorous stirring, ball homogenizer, addition of an emulsifier). Subsequently, 5–10 $\mu L$ of the mixture, so prepared, are sprinkled on a cellulose film (Nephrophan) that is approximately 25 $\mu m$ thick. The droplets are allowed to dry for 24 hours.

On the enzyme layer, so prepared, approximately 10 $\mu L$ of a solution of polymethylene-polyphenyl isocyanate Systanat MR® and ethyl acetate (concentration: 5–10 $\mu L$ isocyanate per 10 mL of ethyl acetate), covered with a second Nephrophan film and rolled to form a firm bond. The sandwich membrane, so formed, is sprinkled on each side with 5–10 $\mu L$ cellulose nitrate solution (solvent: acetone or ethyl acetate concentration of the solution: 0.15–0.05%). The cellulose nitrate is allowed to dry for 1–2 minutes at room temperature.

EXAMPLE 2

Immobilization of lactate oxidase

To 0.5 mL of a Syspur K 8010® solution (0.5 g in 100 mL acetone), 200 units of lactate oxidase are added and homogenized. The mixture (5–10 $\mu L$) is transferred to a cellulose membrane (for example, Nephrophan) 25 $\mu m$ thick and dried for about 1 minute at room temperature. On this enzyme layer, 10 $\mu L$ of a solution of polymethylene polyphenylisocyanate (Systanat MR®) and ethyl acetate (5–10 $\mu L$ in 10 mL) are transferred. The layer is covered with a further cellulose membrane and rolled to form a firm bond.

The sandwich membrane, so formed, is sprinkled on each side with 5–10 $\mu L$ of cellulose nitrate solution (solvent: acetone or ethyl acetate. concentration of the solution: 0.15–0.05). The cellulose nitrate solution is allowed to dry for -2 minutes at room temperature.

EXAMPLE 3

Oxidation of Interfering Substances with $H_2O_2$ Under the Influence of POD and with Destruction of E $H_2O_2$ by Potassium Hexacyanoferrate (II) or Catalase To determine the glucose content, 2 mL of hypotonic phosphate buffer (3 mM $KH_2PO_4$; 10 mM $Na_2HPO_4 \cdot 2 H_2O$; 10 mM $NaF$; 1 mM $Na_2EDTA \cdot 2 H_2O$; 20 mM $KCl$) are added to the measurement cell of the glucometer GKM 01 (made by ZWG Berlin GDR) and 50 $\mu L$ of the solution to be measured are added The glucometer is calibrated against the glucose standard (5.5; 11 and 22 mM) in the aforementioned buffer.

When measuring the glucose content of a pure glucose solution (4.25 mM). the measured value is increased by about 100% by the presence of vanillin (4.25 mM glucose: 3.3 mM vanillin).

To oxidize the interfering substance, the solution is pretreated outside of the measurement cell with $H_2O_2$. The sample (500 $\mu L$) is mixed with 10 $\mu L$ of 0.5 mM $H_2O_2$ and 40 units of POD. After a reaction time of 10 minutes, the excess $H_2O_2$ is destroyed by the addition of 500 $\mu L$ of a 20 mM potassium hexacyanoferrate (II) solution. Interference with the subsequent glucose measurement is prevented by the use of the cellulose nitrate-modified glucose oxidase (GOD) sandwich membrane. A different possibility for destroying the excess hydrogen peroxide is the use of catalase. To 500 $\mu L$ of the sample solution, mixed with POD and hydrogen peroxide, 10 $\mu L$ of a catalase suspension (100 units) are added after 10 minutes. The sample is measured after a further 10 minutes.

An increase in the value measured during the glucose determination as a result of the interfering substances is prevented in this manner. The same results are obtained from measuring a pure glucose solution and a vanillin-containing glucose solution (each 4.25 mM), which were pre treated according to the method given.

EXAMPLE 4

Determination of Glucose in Urine

Per square centimeter, the enzyme membrane contains 45 units of glucose oxidase in polyurethane. It is surrounded on both sides by a cellulose dialysis membrane that is covered with cellulose nitrate. The platinum indicator electrode, which is directly on the enzyme-sandwich membrane, is polarized to +600 mV relative to the reference electrode, so that the hydrogen peroxide formed during the glucose oxidation can be detected as the measurement signal.

To the hypotonic phosphate buffer, which is used for the blood glucose measurement (3 mM $KH_2PO_4$, 10 mM $Na_2HPO_4 \cdot 2 H_2O$, 10 mM $NaF$, 1 mM $Na_2EDTA \cdot 2H_2O$ and 20 mM $KCl$), 2 mM $K_3[Fe(CN)^6]$ is added as oxidizing agent for urine measurements. For the manual urine glucose measurement, 2 mL of the above buffer solution are added to the measurement cell of the calibrated glucometer GKM 01. The addition 50 μL of undiluted urine follows immediately afterwards. Within 6 seconds, the glucose concentration is shown by the digital display of the GKM 01. Because of the oxidation of the reducing substances by the potassium hexacyanoferrate III added to the measurement cell and the prevention of diffusion of the potassium hexacyanoferrate II formed [$K_4FE(CN)_6$] by the modification of the cellulose, it is possible largely to eliminate distortions due to cooxidation. When hypotonic buffer is used without $K_3[Fe(CN)_6]$ and unmodified GOD membrane for uric acid, a 30% higher glucose value is simulated. This interference can be reduced to 3% by measurement with the instruments ADM 300-Glucose VI and ECA 20 (made by PGW Medigen, GDR) with the above system. Up to 20 mM of ascorbic acid cause no increase in the urine glucose signal.

In the case of the continuous flow through measurement (ADM 300, Glucose ECA 20), the urines are diluted 1:50 to 1:100 with the $K_3[Fe(CN)_6]$ containing buffer before the analysis.

EXAMPLE 5

Lactate Determination

A nitrocellulose-modified LOD (lactate oxydase) membrane is placed before the Pt indicator electrode of the Pt-Ag/AgCl sensor of the glucometer, which is polarized to +600 mV for the andic oxidation of the $H_2O_2$ formed in the enzyme reaction. To the measurement portion (0.1 moles/L phosphate buffer pH 7.0) 1 mM $K_3[Fe(CN)_6]$ is added. This solution (2 mL) is added to the measurement cell of the glucometer. After the zero point adjustment, the calibration is carried out with 20 μL quantities of 1, 2, 5, 10 and 20 mmoles/L standard lactate solution. The blood, plasma or serum sample, which is to be analyzed, is then placed in the measurement cell and the wanted value is read on the glucometer.

We claim:

1. A method for preparing a composite, multilayer membrane, which comprises uniformly dispersing one or more enzymes in a liquid solution of a polyurethane, applying droplets of the solution with the dispersed enzyme therein to a first cellulose membrane to form an enzyme film layer, drying the so applied solution, and bonding with a liquid adhesive a second cellulose membrane to the dried solution.

2. The method of claim 1, wherein said liquid adhesive is a diisocyanate, triisocyanate, or polyiisocyanate compound.

3. The method of claim 1, further comprising coating said first and said second cellulose membranes with cellulose nitrate, and drying said cellulose nitrate, prior to or after the cellulose membrane is combined with the enzyme film layer.

4. The method of claim 1, wherein said one or more enzymes is one or more oxidase of glucose, lactate, glutamate, sarcosine, urate, and mutarotase.

5. The method of claim 1, wherein the maximum size of a cellulose layer is 25 μm.

6. The method of claim 1, wherein the maximum thickness of the entire electrode is 25 μm.

7. The method of claim 1, wherein the maximum particle size of said one or more enzymes is 15 μm.

8. The method of claim 1, wherein the maximum particle size of the one or more enzymes is 1 μm.

* * * * *